United States Patent [19]

Yasuhara et al.

[11] Patent Number: 4,568,373
[45] Date of Patent: Feb. 4, 1986

[54] SOIL AMENDMENT MATTERS

[75] Inventors: Minoru Yasuhara, Zushishi; Yoshinobu Yagyu, Fujishi, both of Japan

[73] Assignee: Chissoasahi Fertilizer Co. Ltd., Tokyo, Japan

[21] Appl. No.: 497,064

[22] Filed: May 23, 1983

Related U.S. Application Data

[63] Continuation of Ser. No. 213,735, Dec. 5, 1980, abandoned.

[30] Foreign Application Priority Data

Dec. 8, 1979 [JP] Japan ................................ 54-159631

[51] Int. Cl.⁴ ............................................ C05F 11/08
[52] U.S. Cl. ................................................ 71/6; 71/9; 71/28; 71/903; 71/904
[58] Field of Search ...................... 71/28, 903, 904, 6, 71/9

[56] References Cited

U.S. PATENT DOCUMENTS 2,791,496  5/1957  Rice ..................................... 71/904

OTHER PUBLICATIONS

Yamaguchi et al., "Microbial . . . Soil", *Soil Biol. & Biochem.*, 1978, 10 (6), pp. 503–508.
Yasuhara, "Influence of CDU on Soil Microflora", NDHZ, 1969, pp. 78–83 (Japan).

*Primary Examiner*—Ferris H. Lander
*Attorney, Agent, or Firm*—Fred Philpitt

[57]  ABSTRACT

A soil amendment matter is provided which is effective for preventing soils from suffering from injuries due to continuous cropping. This matter is obtained by adding a soil to a medium containing 2-oxo-4-methyl-6-ureidohexahydropyrimidine (OMPU) as nutrient and subjecting the mixture to an aerobic cultivation treatment. Further the matter can contain OMUP as an additional effective component. These matters can be adsorbed on an adsorbent and used.

22 Claims, No Drawings

SOIL AMENDMENT MATTERS

This application is a continuation of Ser. No. 213,735, filed on Dec. 5, 1980, and now abandoned.

BACKGROUND OF THE INVENTION

This invention relates to an improvement in soils. Particularly it relates to soil amendment matters effective for improving soils which suffer from injuries due to continuous cropping which means herein repeated cultivations of the same crop on the same field.

Recently, in most of the districts where leafy vegetables or fruit vegetables are produced, continuous cropping of specified crops have often been carried out from a necessity of management, and as the number of years of continuous cropping increases, the injuries due to continuous cropping occur frequently, and this has been raising a serious problem in cultivation.

Representative injuries due to continuous cropping are Fusarium-wilt of watermelon, melon, cucumber or the like, damping off of tomato, pepper or the like, other wilts of Japanese radish, strawberry or the like, clubroot of Chinese cabbage, turnip, salting greens, cabbage or the like. Most of pathogenic microorganisms causing these diseases belong to fungi such as Fusarium, Plasmodiophora, etc.

As for the measures for preventing the injuries due to continuous cropping, treatments such as spray of fungicides, fumigation, etc. have generally been carried out. However, these methods have various drawbacks in that chemicals used neither selectively inhibit nor kill pathogenic fungi alone, but they act inhibitorily also on non-pathogenic microorganisms including essential ones e.g. nitrifiers, ammonifiers, or when pathogenic microorganisms again invade soils which have been sterile after the treatments, they propagate easily, resulting contrarily in more violent damages, and moreover, a certain period of time is often required till the chemicals after the treatments vanish and become harmless to crops or humans and domestic animals.

Thus, the present invention is to provide a method for preventing injuries due to continuous cropping, by suppressing pathogenic fungi without inhibiting essential microorganisms, and inflicting no damages on crops or humans and domestic animals. In the studies for attaining the object, the present inventors have found that when 2-oxo-4-methyl-6-ureidohexahydropyrimidine (which will be hereinafter referred to as "OMUP") is applied to soils, the injuries due to continuous cropping are sometimes alleviated. However, the effect attained by such a method is unstable and it generally takes considerable days till the actual effect is developed. The injuries of crops due to continuous cropping generally occur as a result of invasion of pathogenic fungi at a certain limited period of growth of crops (very often at the initial period of growth); hence it is important for preventing the injuries to protect the roots of crops from pathogenic fungi for a definite period during the growth. Thus, a soil amendment matter is desired which does not require a long time in developing the effect of preventing the injuries due to continuous cropping; brings about a reliable preventing effect; and makes it easy to apply the matter at an adequate time and effectively in accordance with cultivation plan. In this respect, the object cannot be attained by a single application of OMUP, and advent of a more effective and more reliable matter which makes it possible to prevent the injuries due to continuous cropping has been desired As a result, the present inventors have found that a product of a cultivation treatment carried out under aerobic conditions using OMUP as main organic nutrient is effective, and further, a product obtained by making OMUP coexistent with the above product is more effective.

SUMMARY OF THE INVENTION

An aspect of the present invention resides in a soil-amendment matter comprising as an effective component, a product obtained by adding a soil to a medium containing OMUP as organic nutrient and subjecting the mixture to an aerobic cultivation treatment.

Another aspect of the present invention resides in a soil amendment matter comprising as effective components, a product obtained by adding a soil to a medium containing OMUP as organic nutrient and subjecting the mixture to an aerobic cultivation treatment, and further OMUP added to the above product so that the total of the amount of this OMUP and that of OMUP remaining in the above product is almost equal to the amount of OMUP initially contained in the medium. The organic nutrient referred to herein means both nitrogen source and carbon source.

PREFERRED EMBODIMENTS OF THE INVENTION

As for the medium, materials consisting of OMUP, inorganic nutrient substances and water are used as a basal medium, and a trace of extracts such as yeast extracts as a mixture of various vitamines may be added to the above basal medium. The amount of these extracts added is preferably 0.02% by weight or less based on the medium, and more amounts are unnecessary. The content of OMUP in the medium is suitably in the range of 0.05 to 1%. An example of the basal medium is as follows:

OMUP 0.5 to 10 g, $KH_2PO_4$ 1 to 2 g, $M_gSO_4.7H_2O$ 1 to 3 g,

KCl 0.1 to 2 g, $FeSO_4$ 0.001 to 0.1 g, tap water 1 l, pH 6.0 to 7.5.

The soil to be added may be those under conditions where a wide variety of aerobic microorganisms are alive, and preferably those of fertile cultivated soils having a high content of organic matters. The soil is not always limited to those of cultivated soils, but the sediments of rivers or activated sludges which are similar to the microflora of soil and wherein a wide variety of microorganisms are alive, may be used. As for these soils, if a small amount of OMUP (about 1 to 2 g based on 1 Kg of the soils) is added to them in advance of using them and the mixture is allowed to stand for a certain period e.g. about 20 days, then the subsequent cultivation treatment is more effective. The amount of soils added is preferably in the range of 0.01 to 0.5% by weight. Soils may be added as they are, but a supernatant liquid obtained after shaking soils with water in an amount of 2 to 10 times the volume of soils, followed by still standing may also be added. In this invention, it is to be noted that the addition of soils includes that of such a supernatant liquid.

The temperature of the cultivation treatment is in the range of 15° to 45° C., preferably 20° to 35° C., and the period is in the range of 3 to 30 days.

In order to carry out the aerobic cultivation treatment, the materials may be only allowed to stand under such conditions that the surface area of the medium per unit volume is broader and its contact with air is more efficient, but continuous shaking or agitation under aeration may be also employed.

After the aerobic cultivation treatment, OMUP in the medium will vanish or be reduced. If the soils added are not under the above-mentioned conditions and unsuitable (as in the case of soils soon after an excessive application of fungicides or calcined soils although such cases are rare), then OMUP is hardly reduced; hence it is difficult to expect the effectiveness of the present invention. In order to foresee such unsuitable soils, colorimetry of OMUP is employed. The procedure is as follows: To a medium containing 0.07% of OMUP is added 0.2% of a soil as a sample, and the mixture is subjected to cultivation treatment under shaking at 30° C., for 10 days. Thereafter, the content of OMUP in the filtrate can be determined according to the following colorimetry of OMUP:

A solution of p-dimethylaminobenzaldehyde dissolved in 3.6 N sulfuric acid solution so as to give 2.2% (w/v) is heated together with an OMUP-containing solution (probe solution), at 80° C. for 30 minutes to show a red color. Thus, it is possible to correctly measure the content of OMUP at a wave length of 530 mm, by way of a calibration curve prepared in advance. The practice of the determination carried out hereinafter is as follows:

The probe solution, if necessary, is adjusted by dilution so as to give OMUP in the range of 10 to 200 ppm; 5 ml of the above solution of p-dimethylaminobenzaldehyde is added to 5 to 10 ml of the probe solution; if necessary, distilled water is added to make the total amount 15 ml; and the resulting material is heated in a test tube in a water bath at 80° C., whereby color is developed.

The soils used in the present invention are those wherein 35% or more, preferably 50% or more of OMUP has already vanished according to the determination under the above-mentioned conditions. The matter thus obtained by the aerobic cultivation treatment is effective for the prevention of the injuries due to continuous cropping, as the object of the present invention. The whole of a residue obtained by removing non-functional water from the material after the cultivation treatment will be herein referred to as "composition after the treatment". The water-containing material after the cultivation treatment and the composition after the treatment refer to substantially the same material in the function and effectiveness. In the case of the composition after the treatment, if conditions such as soils added, composition of the medium, conditions of the cultivation treatment, etc. are suitable, almost all of the OMUP contained in the medium will have vanished. By applying such a composition after the treatment, as it is, to cultivated soils, the effect of fully preventing the injuries due to continuous cropping will be exhibited.

However, when OMUP in almost the same amount as that of OMUP contained in the initial medium is added to and mixed with the composition after the treatment and the mixture is applied, the effect of preventing the injuries due to continuous cropping is more improved, and also the effect is maintained for a longer time. In this case, if OMUP is remaining in the composition after the treatment due to the conditions of cultivation treatment, etc., then the amount of OMUP added may be adjusted. It may be sufficient if the OMUP added and mixed is coexistent with the composition after the treatment, at the time of application; hence they may be separately applied to cultivated solids in place of the above-mentioned addition and mixing.

The details of the mechanism by which the application of such a composition after the treatment or a product having OMUP added thereto exhibits the effect of preventing the injuries due to continuous cropping have not yet been clarified, but the present inventors presume the mechanism as follows: The diseases due to the pathogenic fungi are suppressed only slowly and uncertainly if such suppression is relied only to microorganisms increased by applying OMUP to a soil in a natural environment. In such a situation, the suppressive action is artificially enhanced by the soil amendment matter of the present invention. Namely, by applying to a soil, a product obtained by adding a small amount of soil to a medium containing OMUP, followed by subjecting the resulting mixture to a cultivation treatment, a large amount of microorganisms enough not to be governed by natural environmental factors, are fixed to rhizosphere. Further, the reason that the product obtained by adding OMUP to the composition after the treatment is more effective is that when the product is applied, OMUP is much more useful in the growth of the effective microorganisms which are adaptable to the natural environment, that is, the composition after the treatment and the OMUP to be made coexistent therewith function synergistically to enhance the effect of preventing the injuries due to continuous cropping. This fact is shown in Examples mentioned later. On the other hand, OMUP is also used as a nitrogenous fertilizer; hence in order to make the fertilizer effect sufficient, an amount of OMUP exceeding the above-mentioned amount added and mixed may be used.

As for the form in which the composition after the treatment or the product having OMUP added thereto is applied, those after the cultivation treatment containing a large amount of water may be used as they are, but those obtained by removing most of water by centrifugal separation or the like may be also used. Those obtained by causing them to be adsorbed to adsorbents are more preferable for enhancing practical properties in storage, transportation, application, etc. Such an adsorption is also preferable in the case of the product having OMUP added to the composition after the treatment, since the coexistent state of the above components is well maintained. As such adsorbents, those having fine pores and water-retainability are preferable. Mineral ones are particularly preferable. Concretely, calcined vermiculite, pearlite, etc. are illustrated. As organic adsorbents, those consisting of synthetic high molecular weight substances, difficultly decomposable organic substances such as those composed mainly of lignin, etc. are illustrated. In the case where the composition after the treatment or this composition plus OMUP are adsorbed to adsorbents, even if they are sprayed on and mixed with adsorbents, in a state, as it is, where they contain a large amount of water after the cultivation treatment, no particular operations such as drying are required, but storage is possible and handlings such as transportation, application, etc. are easy.

The soil amendment matters of the present invention are effective for preventing injuries due to continuous cropping of various crops.

The present invention will be illustrated by way of the following Examples:

EXAMPLE 1

To 25 l of a basal medium (OMUP 3 g, $KH_2PO_4$ 2 g, $MgSO_4.7H_2O$ 2.5 g, KCl 0.5 g, $FeSO_4$ 0.01 g, tap water 1 l, pH 6.8), was added 12 g of a material obtained by treating a volcanic ash soil in Miura Peninsula, Kanagawa Prefecture, Japan, as follows: 90 mg of OMUP was added to 100 g of the soil; water in an amount corresponding to 60% of the maximum water-holding capacity thereof was then added; and the mixture was allowed to stand at 25° C. for 30 days.

The mixture of the medium with the material was subjected to a cultivation treatment under aeration agitation at 25° C. for 5 days and the resulting composition was subjected to centrifugal separation, followed by suspending the collected material in 1 l of tap water to obtain a soil amendment matter (I). Further, 1 l of this matter (I) was sprayed on and mixed with 1 Kg of calcined vermiculite (capable of adsorbing and retaining 510 g of water per 100 g thereof) to obtain a soil amendment matter (II) having a water content of 50%. In addition, as a result of the determination, it was found that OMUP in the soil amendment matter (I) vanished and was hardly contained therein.

EXAMPLE 2

To 10 l of a medium (OMUP 10 g, $KH_2PO_4$ 1.0 g, $MgSO_4.7H_2O$ 1.0 g, KCl 0.3 g, $FeSO_4.7H_2O$ 0.01 g, tap water 1 l, pH 6.5) was added 50 ml of a supernatant liquid obtained by shaking 20 g of a material (obtained by applying to an alluvial soil collected in Fuji City, Shizuoka Prefecture, Japan, 100 Kg of OMUP per 10 a, twice a year, under field condition), with 100 ml of sterilized water, followed by still standing for 5 minutes. The resulting mixture was subjected to aeration cultivation treatment at 30° C. for 12 days to obtain a soil-amendment matter (III). Further, to 10 l of this matter (III) was added 58 g of OMUP, and the mixture was sprayed on and mixed with 10 g of vermiculite to obtain a soil-amendment matter (IV) having a water content of 50%. In addition, 10 l of this soil-amendment matter (III) contained 42 g of OMUP.

EXAMPLE 3

To 1 l of the same as the above-mentioned soil-amendment matter (I) was added 600 g of OMUP, and the mixture was then mixed with 400 g of a calcined pearlite (capable of adsorbing and retaining 950 g of water per 100 g thereof) to obtain a soil-amendment matter (V).

USE EXAMPLE 1

To 1 Kg of an alluvial soil notably infested with *Fusarium oxysporum* f.cucumerinum due to continuous cropping of cucumber was added and mixed OMUP, the soil-amendment matter (II) or (IV) of the present invention, respectively, in amounts indicated in Table 1, and the water content of these mixtures were adjusted to 60% of the maximum water-holding capacity, followed by still standing at a dark place at 30° C.

The soils were collected with the increase of time, and *Fusarium oxysporum* f.cucumerinum was measured on a potato-agar medium having pentachloronitrobenzene added, according to plate-dilution method. The results are shown in Table 1.

TABLE 1

Change in Fusarium population (per g of dry soil) in a soil on which continuous cropping of cucumber was carried out.

| Treated section | Amount added (g) | Amount of OMUP in additive (g) | Fusarium population (unit: thousand) | | |
|---|---|---|---|---|---|
| | | | 0 day | 15th day | 30th day |
| 1. No addition | — | — | 16 | 19 | 17 |
| 2. OMUP | 0.2 | 0.2 | " | 12 | 7.9 |
| 3. " | 1.0 | 1.0 | " | 11 | 3.8 |
| 4. Amendment matter (II) of present invention | 5.0 | 0 | " | 7.6 | 2.1 |
| 5. Amendment matter (II) of present invention | 10.0 | 0 | " | 5.7 | 1.9 |
| 6. Amendment matter (IV) of present invention | 5.0 | 0.025 | " | 7.9 | 2.6 |
| 7. Amendment matter (IV) of present invention | 10 | 0.05 | " | 5.1 | 1.2 |
| 8. Amendment matter (IV) of present invention | 40 | 0.2 | " | 4.8 | 0.8 |
| | 200 | 1.0 | " | 2.9 | 0.6 |

USE EXAMPLE 2

Tomato was cultivated on a soil notably infested with *Fusarium oxysorum* f.lycopersici due to continuous cropping of tomato, and on a soil close to the above soil but not subjected continuous cropping, respectively, under the following conditions:

(1) Test scale: a section of 5 m×2 m, in duplicate
(2) Amount of fertilizer applied:

$N=P_2O_5=K_2O=0.4$ Kg/test section

Ammonium sulfate, superphosphate and potassium sulfate were used as fertilizers, and the nitrogen content having OMUP added was adjusted by reducing the amount of ammonium sulphate.

(3) Planting density:
  one plant/0.8 m² (13 plants/one test section)
(4) Test section and amount applied: indicated in Table 2
(5) Investigation method: the number of infected plants and the yield of the fruit were observed. Further, Fusarium population was observed before the start of the test and just after the harvest in the same manner as in Use example 1.

The results are shown in Table 2.

TABLE 2

Effect on Fusarium population in tomato cultivation

| Soil | Treated section | % of*[1] plants infected | Yield Kg | Yield %*[2] | Fusarium population (in 1 g of dry soil, unit: thousand) Before application | Fusarium population (in 1 g of dry soil, unit: thousand) Inst. after harvest |
|---|---|---|---|---|---|---|
| Soil not subjected to continuous cropping | 1. No addition (section of single use of chemical fertilizer) | 12 | 108 | 100 | 2.9 | 4.2 |
| | 2. OMUP 300 g | 0 | 112 | 103 | " | 1.2 |
| | 3. Soil amendment matter (I) 500 g | 0 | 118 | 109 | " | 0.8 |
| | 4. Soil amendment*[3] matter (V) 1 Kg | 0 | 120 | 111 | " | 0.5 |
| Soil subjected to continuous cropping | 1. No addition (section of single use of chemical fertilizer) | 89 | 21 | 19 | 12 | 21 |
| | 2. OMUP 300 g | 15 | 80 | 74 | " | 6.7 |
| | 3. Amendment matter of present invention (I) 500 g | 2 | 102 | 94 | " | 2.1 |
| | 4. Amendment*[3] matter of present invention (V) 1 Kg | 0 | 110 | 102 | " | 0.8 |

*[1](number of plants infected/number plants planted) × 100
*[2]Non-addition section of soil not subjected to continuous cropping
*[3]1 Kg of soil amendment matter (V) contains 300 g of OMUP.

USE EXAMPLE 3

1 Kg of a volcanic ash soil notably infested with *Plasmodiophora brassicae* due to continuous cropping of Chinese cabbage was placed in a vessel of 30 cm × 8 cm × 15 cm, and ammonium sulfate, superphosphate and potassium sulfate, each 0.1 g, were added, and further, 2 g of the soil amendment matter (I) or 5 g of the soil amendment material (IV) was added and mixed, followed by seeding the mixture with 10 seeds of Chinese cabbage. Cultivation was carried out in a greenhouse at 20° C. ±5° C. for 40 days to observe the percentage of plants infected, of *Plasmodiophora brassicae*. The test was carried out in triplicate, and the percentage of plants infected, of *Plasmodiophora brassicae* in 30 plants each test section is shown in Table 3.

TABLE 3

Effect on *Plasmodiophora brassicae*

| Treated section | Non-treatment | Soil amendment matter (I) | Soil amendment matter (IV) |
|---|---|---|---|
| Percentage of plants infected, of *Plasmodiophora brassicae* | 90% | 10% | 7% |

USE EXAMPLE 4

On test sections, each 10 m × 2.5 m, of a cultivated soil of a volcanic ash soil infested with *Plasmodiophora brassicae* due to continuous cropping of cabbage, a fertilizer and the soil amendment matter (III) of the present invention were applied on July 27, and seedlings of cabbage were planted on August 1. The soil amendment matter (III) was uniformly sprayed in an amount of 1 l per m², i.e. 25 l each section, and plowed into the soil and OMUP applied as a fertilizer at the same time. Harvest was carried out on October 25, and the effects of the soil amendment matter (III) upon the extent of attack of the disease and the yield of cabbage were observed. The results are shown in Table 4.

In addition, the amounts of N, $P_2O_5$ and $K_2O$ as fertilizers were each 625 Kg per one section, and further, 2.5 Kg of slaked lime was applied on each section, and the initial pH was adjusted to 7.1. In the sections (2) and (3) where OMUP was used as N source, the N source was totally supplemented by OMUP, and OMUP of 8 to 20 mesh was used. Superphosphate and potassium sulfate were used as $P_2O_5$ and $K_2O$, respectively. In the section (3), the amount of OMUP originating from the amendment matter (III) was subtracted from the amount of OMUP applied as fertilizer.

TABLE 4

Effects upon *Plasmodiophora brassicae* of cabbage

| Section | Yield* (per 10a) Kg | Average weight of loaf g | Percentate of plants infected slight | Percentate of plants infected light | Percentate of plants infected severe |
|---|---|---|---|---|---|
| (1) Conventional section High degree compound fertilizer 15-15-15 | 465 | 865 | 10 | 5 | 95 |
| (2) Section of single use of OMUP | 1,328 | 898 | 23 | 35 | 28 |
| (3) Section of OMUP and amendment matter (III) of | 2,240 | 916 | 41 | 22 | 8 |

TABLE 4-continued

| | Effects upon *Plasmodiophora brassicae* of cabbage | | | | |
|---|---|---|---|---|---|
| | Yield* (per 10a) | Average weight of loaf | Percentate of plants infected | | |
| Section | Kg | g | slight | light | severe |
| present invention | | | | | |

*Harvest was directed to products having a weight of 700 g or more.

What is claimed is:

1. A soil amendment matter comprising as an effective component, a culture obtained by adding 0.01 to 0.5% by weight of a soil to an aqueous nutrient medium containing 0.05 to 1% by weight of 2-oxo-4-methyl-6-ureidohexahydropyrimidine (OMUP) and thereafter subjecting the resulting mxiture to an aerobic cultivation treatment at 15°–45° C. for 3–30 days.

2. A soil amendment matter obtained by adding 2-oxo-4-methyl-6-ureidohexahydropyrimidine to said culture of claim 1 after said cultivation treatment.

3. A soil amendment matter according to claim 1 wherein 1–2 gram of OMUP per 1 Kg of soil is added to the soil and allowed to stand with said soil for a period of time before the start of the aerobic cultivation treatment.

4. A soil amendment matter according to claim 1 wherein the OMUP will be reduced or vanish at the end of said cultivation treatment.

5. A soil amendment matter according to claim 1 wherein said culture is adsorbed on an adsorbent.

6. A soil amendment matter according to claim 1 wherein said soil is a fertile cultivated soil having a high content of organic matters.

7. A soil amendment matter obtained by adding almost the same amount as that of OMUP contained in the initial medium, of 2-OXO-4-methyl-6-ureidohexahydropyrimidine to said culture of claim 1 after said cultivation treatment.

8. A method of inhibiting pathogenic microorganisms which comprises applying to a cultivation soil, a soil amendment matter comprising as an effective component, a culture obtained by adding 0.01 to 0.5% by weight of a soil to an aqueous nutrient medium containing 0.05 to 1% by weight of 2-oxo-4-methyl-6-ureidohexahydropyrimidine and subjecting the resulting mixture to an aerobic cultivation treatment at 15°–45° C. for 3–30 days.

9. A method of inhibiting pathogenic microorganisms, according to claim 8 wherein said soil amendment matter comprises said culture plus added 2-oxo-4-methyl-6-ureidohexahydropyrimidine.

10. A method according to claim 8 wherein 1–2 g of OMUP per 1 Kg of soil is added to the soil and allowed to stand with said soil for a period of time before the start of the aerobic cultivation treatment.

11. A method according to claim 8 wherein the OMUP will be reduced or vanish at the end of said cultivation treatment.

12. A method according to claim 8 wherein said culture is adsorbed on an adsorbent.

13. A method according to claim 8 wherein said cultivation soil is a fertile cultivated soil having a high content or organic matter.

14. A method of inhibiting pathogenic microorganisms according to claim 8 wherein said soil amendment matter comprises said culture plus almost the same amount as that of OMUP contained in the initial medium of 2-oxo-4-methyl-6-ureidohexahydropyrimidine.

15. An agricultural innoculant comprising a concentration of bacteria having the characteristic of reducing the fungi population upon application to soil, said innoculant comprising as its effective component the product obtained by aerobically cultivating at 15°–45° C. for 3–30 days an admixture comprising 2-oxo-4-methyl-6-ureidohexahydropyrimidine (OMUP) and a quantity of soil.

16. An innoculant according to claim 15 wherein said product is obtained by adding 0.01 to 0.5% by weight of a soil to an aqueous medium containing 0.05 to 1% by weight of OMUP and thereafter subjecting the resulting mixture to an aerobic cultivation treatment.

17. An innoculant according to claim 15 wherein said product includes OMUP added after the completion of said cultivation treatment.

18. An ihnoculant according to claim 15 wherein 1–2 g of OMUP per 1 Kg of soil is added to the soil and allowed to stand with said soil for a period of time before the start of the aerobic cultivation treatment.

19. An innoculant according to claim 15 wherein the OMUP will be reduced or vanish at the end of said cultivation treatment.

20. An innoculant according to claim 15 wherein said culture is adsorbed on an adsorbent.

21. An agricultural innoculant according to claim 15 wherein said quantity of soil is a fertile cultivated soil having a high content of organic matters.

22. An innoculant according to claim 15 wherein said product includes almost the same amount as that of OMUP contained in the initial medium of OMUP added after the completion of said cultivation treatment.

* * * * *